US00PP31153P2

(12) United States Plant Patent
Smit

(10) Patent No.: US PP31,153 P2
(45) Date of Patent: Dec. 3, 2019

(54) ***TRADESCANTIA* PLANT NAMED 'EC-TRADE-1809'**

(50) Latin Name: *Tradescantia zebrina*
Varietal Denomination: EC-TRADE-1809

(71) Applicant: Obcd Jacob Smit, Sappemeer (NL)

(72) Inventor: Obcd Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/350,768

(22) Filed: Jan. 4, 2019

(51) Int. Cl.
*A01H 5/00* (2018.01)

(52) U.S. Cl.
USPC ..... Plt./263.1

(58) Field of Classification Search
USPC ..... Plt./263.1
CPC ..... A01H 5/00
See application file for complete search history.

*Primary Examiner* — Annette H Para

(57) ABSTRACT

A new cultivar of *Tradescantia* plant named 'EC-TRADE-1809' that is characterized by silver and purple leaves that have a sharp definition between the silver and purple areas, short internodes and a compact habit.

1 Drawing Sheet

Botanical classification: *Tradescantia zebrina.*
Variety denomination: 'EC-TRADE-1809'.

BACKGROUND OF THE INVENTION

The present invention relates to a new and distinct cultivar of *Tradescantia* plant botanically known as *Tradescantia zebrina* and hereinafter referred to by the cultivar name 'EC-TRADE-1809'.

'EC-TRADE-1809' originated from the crossing of the female or seed parent, an unnamed *Tradescantia zebrina* cultivar and the male or pollen parent, an unnamed *Tradescantia zebrina* cultivar. The crossing was conducted in 2015 in Sappemeer, Netherlands. The resulting seeds were subsequently planted and grown. The cultivar 'EC-TRADE-1809' was selected by the inventor in 2016 in a controlled environment as a single plant within the progeny of the stated cross in a cultivated area of Sappemeer, Netherlands.

Asexual reproduction of the new cultivar 'EC-TRADE-1809' first occurred by stem cuttings in 2016 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tradescantia* cultivar 'EC-TRADE-1809'. These traits in combination distinguish 'EC-TRADE-1809' as a new and distinct cultivar apart from other existing varieties of *Tradescantia* known by the inventor.

1. *Tradescantia* 'EC-TRADE-1809' exhibits silver and purple leaves that have a sharp definition between the silver and purple areas.
2. *Tradescantia* 'EC-TRADE-1809' exhibits short internodes.
3. *Tradescantia* 'EC-TRADE-1809' exhibits a compact habit.

The closest comparison cultivars are plants of the species *Tradescantia pendula* (not patented) and plants of the species *Tradescantia carnivale* (not patented). 'EC-TRADE-1809' is distinguishable from *Tradescantia pendula* by the following characteristics:

1. *Tradescantia* 'EC-TRADE-1809' exhibits silver and purple leaves that have a sharp definition between the silver and purple areas. In comparison, the leaves of *Tradescantia pendula* are light and dark purple in color.
2. The leaves of *Tradescantia* 'EC-TRADE-1809' are wider than the leaves of *Tradescantia pendula*. The leaves of *Tradescantia pendula* are more elongated than the leaves of 'EC-TRADE-1809'.

'EC-TRADE-1809' is distinguishable from *Tradescantia carnivale* by the following characteristics:

1. *Tradescantia* 'EC-TRADE-1809' exhibits silver and purple leaves that have a sharp definition between the silver and purple areas. In comparison, the leaves of *Tradescantia carnivale* are green and pink in color.
2. The leaves of *Tradescantia* 'EC-TRADE-1809' are larger in length and width than the leaves of *Tradescantia carnivale.*

'EC-TRADE-1809' is distinguishable from the female parent plant, by the following characteristics:

1. The leaves of 'EC-TRADE-1809' have a sharp definition between the silver and purple areas. In comparison, the leaves of the female parent plant do not have a sharp definition between the silver and purple areas.
2. The internodes of 'EC-TRADE-1809' are shorter than the internodes of the female parent plant.

'EC-TRADE-1809' is distinguishable from the male parent plant by the following characteristics:

1. The leaves of 'EC-TRADE-1809' have a sharp definition between the silver and purple areas. In comparison, the leaves of the male parent plant do not have a sharp definition between the silver and purple areas.
2. The internodes of 'EC-TRADE-1809' are shorter than the internodes of the male parent plant.

BRIEF DESCRIPTION OF THE DRAWING

The accompanying photograph illustrates the distinguishing traits of *Tradescantia* 'EC-TRADE-1809'. The photograph shows an overall view of an 18 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Tradescantia* cultivar named 'EC-TRADE-1809'. Data was collected in Sappemeer, Netherlands from 18 week old plants grown in a glass greenhouse in 10.5 cm. diameter containers. The time of year was Fall and the temperature range was 18-21 degrees Centigrade during the day and 18-21 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-TRADE-1809' has not been tested under all possible conditions and phenotypic differences may be observed with variations in environmental, climatic, and cultural conditions, however, without any variance in genotype.

Botanical classification: *Tradescantia zebrina* 'EC-TRADE-1809'.

Annual or perennial: Perennial.

Parentage: 'EC-TRADE-1809' is a hybrid of the female parent, an unnamed *Tradescantia zebrina* cultivar and the male parent an unnamed *Tradescantia zebrina* cultivar.

Plant type: Potted plant.

Growth habit: Broad spreading upright.

Plant shape: Spreading to flattened globe shaped.

Suitable container size: 7 cm. pots or larger.

Plant height to top of foliage plane: Average 9.0 cm.

Plant width: Average 18.6 cm.

Vigor: Low to moderate.

Growth rate: Low to moderate.

Low temperature tolerance: 12° Centigrade.

High temperature tolerance: 30° Centigrade.

Propagation: Stem cuttings.

Time to initiate roots: Cuttings are placed directly in growing containers.

Crop time: Approximately 20 weeks in Sappemeer, Netherlands.

Root system: Fibrous.

Plant fragrance: None.

Stem:

- *Branching habit*.—Main branches grow from base with lateral branches.
- *Basal branching*.—Yes.
- *Pinching*.—Not required.
- *Number of main branches per plant*.—Average 13.
- *Number of lateral branches per plant*.—Average 20.
- *Main branch dimensions*.—Average 5.7 cm. in length and 0.35 cm. in diameter.
- *Internode length*.—Average 0.7 cm.
- *Stem shape*.—Rounded.
- *Stem texture*.—Smooth.
- *Stem luster*.—Matte.
- *Stem pubescence*.—Absent.
- *Stem angle*.—Average 70 degrees from vertical.
- *Stem strength*.—Moderately weak.
- *Stem color* (*young*).—145A.
- *Stem color* (*mature*).—146C, tinged 200C.
- *Stem color* (*old*).—N199A.
- *Internode color*.—200C, tinged 146B.

Foliage:

- *Leaf arrangement*.—Distichous.
- *Compound or single*.—Single.
- *Quantity of leaves per lateral branch*.—Average 9.
- *Leaf shape*.—Broad ovate, moderately oblique.
- *Leaf aspect*.—Flat to very slightly concave.
- *Leaf apex*.—Apiculate.
- *Leaf base*.—Oblique, sheathing.
- *Leaf dimensions*.—Average 5.4 cm. in length and 3.4 cm. in width.
- *Sheath dimensions*.—Average 0.6 cm. in length and 0.35 cm. in width.
- *Texture* (*upper surface*).—Glabrous, very velvety.
- *Texture* (*lower surface*).—Glabrous.
- *Leaf luster* (*upper surface*).—Very slightly glossy, very velvety.
- *Leaf luster* (*lower surface*).—Slightly glossy.
- *Pubescence* (*upper surface*).—Sparsely to moderately covered with very short soft hairs, 0.1 cm. in length, color 156D.
- *Pubescence* (*lower surface*).—Absent.
- *Pubescence* (*sheath*).—Densely covered with soft hairs, 0.15 cm. in length, color 156D.
- *Leaf margin*.—Entire.
- *Leaf lobed*.—Not lobed.
- *Leaf rugose*.—Not rugose (both surfaces).
- *Venation pattern*.—Parallel.
- *Young leaf color* (*upper surface*).—191C, toward margin 146A, margins N77C, center 147A.
- *Young leaf color* (*lower surface*).—77A with irregular blotches N77A and 146A to 146B.
- *Mature leaf color* (*upper surface*).—191B, toward margin 147A, margins N77B, center 147A.
- *Mature leaf color* (*lower surface*).—Blotched 77A and 146A.
- *Vein color* (*upper surface*).—147A.
- *Vein color* (*lower surface*).—N77A.
- *Sheath color*.—147D with axial stripes 146 D and N77D.
- *Leaf attachment*.—Sessile.

Flower: 'EC-TRADE-1809' has not produced flowers to date.

Fruit and seed: 'EC-TRADE-1809' has not produced fruit or seed to date.

The invention claimed is:

1. A new and distinct variety of *Tradescantia* plant named 'EC-TRADE-1809' as described and illustrated.

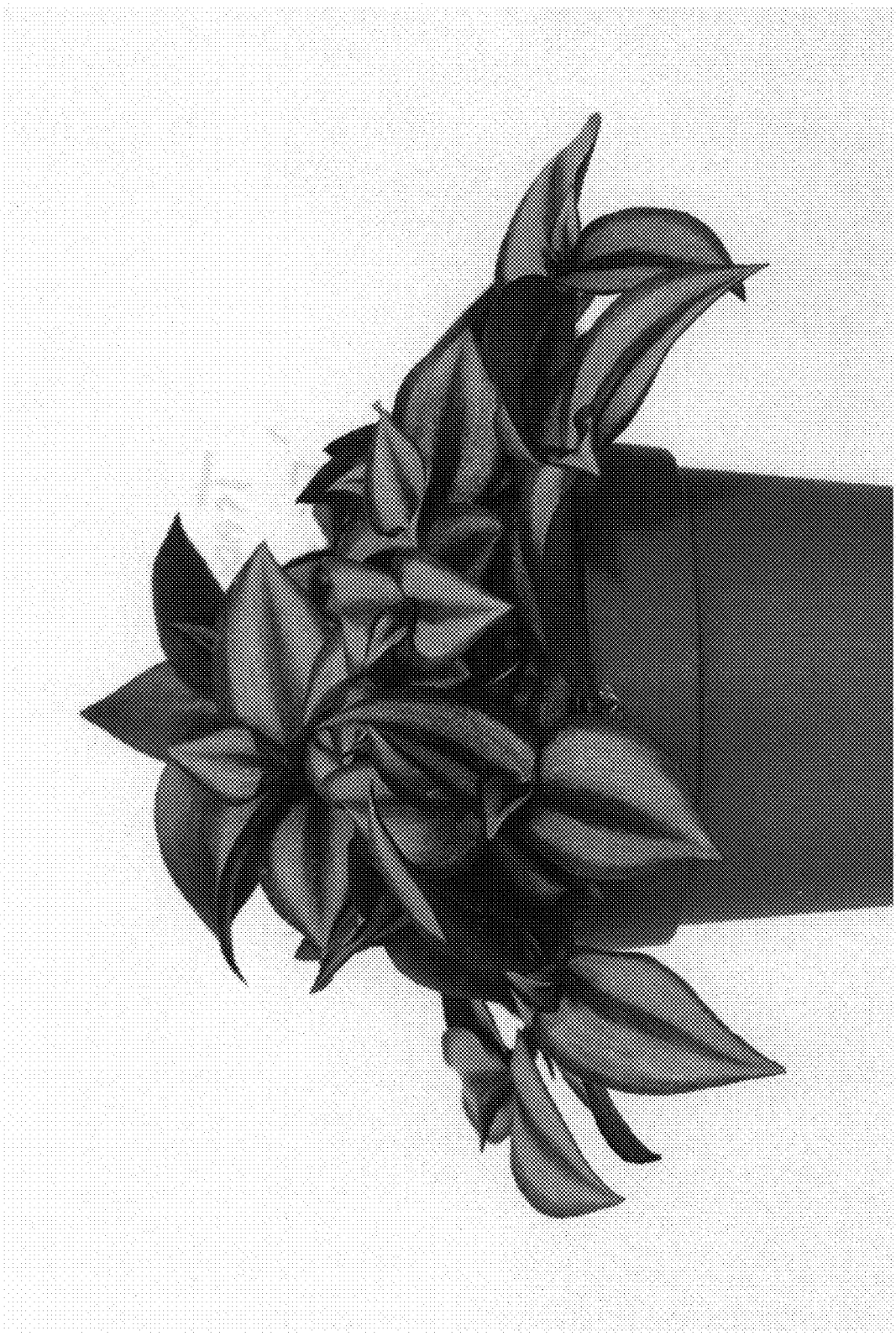

* * * * *